(12) United States Patent
Le

(10) Patent No.: US 7,185,546 B2
(45) Date of Patent: Mar. 6, 2007

(54) SYSTEMS AND METHODS FOR MEASURING BELT TENSION

(75) Inventor: Canh Le, San Jose, CA (US)

(73) Assignee: ASCENX, Milptas, CA (US)

(*) Notice: Subject to any disclaimer, the term of this patent is extended or adjusted under 35 U.S.C. 154(b) by 57 days.

(21) Appl. No.: 10/867,904

(22) Filed: Jun. 14, 2004

(65) Prior Publication Data

US 2005/0274197 A1    Dec. 15, 2005

(51) Int. Cl.
*G01N 29/04*    (2006.01)

(52) U.S. Cl. ........................................ 73/801
(58) Field of Classification Search .............. 73/801
See application file for complete search history.

(56) References Cited

U.S. PATENT DOCUMENTS

| 4,375,180 | A | * | 3/1983 | Scholz | ............ 84/454 |
| 5,435,191 | A | * | 7/1995 | Kawachi | ............ 73/862.41 |
| 5,698,796 | A | * | 12/1997 | Hirano | ............ 73/862.41 |
| 5,877,431 | A | * | 3/1999 | Hirano | ............ 73/862.41 |
| 6,374,168 | B1 | * | 4/2002 | Fujii | ............ 701/45 |
| 2004/0154413 | A1 | * | 8/2004 | Coy et al. | ............ 73/862.453 |

* cited by examiner

*Primary Examiner*—Max Noori
(74) *Attorney, Agent, or Firm*—Tran & Associates

(57) ABSTRACT

Systems and methods for measuring belt tension in a semiconductor processing system include measuring a natural sound or an acceleration of the belt in the semiconductor processing system; digitizing the natural sound or the acceleration; determining the frequency and characterizing the belt tension as a function of the frequency.

20 Claims, 4 Drawing Sheets

SYSTEMS AND METHODS FOR MEASURING BELT TENSION

BACKGROUND

The present invention relates to a belt tension measuring apparatus.

In many belt drive system applications, it is important to optimize belt tension. The purpose of a belt tensioner is to maintain a substantially constant tension in a drive belt. In most applications, the belt connects stationary pulleys. Hence, belt tension can be set by affixing one pulley to a mount having an adjustable linkage to a fixed mounting surface. Automobile engine belts are common examples of this type of system.

In typical power transmission arrangements, a belt is spanned over and around one or more pulleys. Conventionally, to measure a tension of the belt, the belt is pushed downwardly under a predetermined pressure applied by means of a pressure gauge (or manometer) disposed so as to bear against the belt at a predetermined position thereof, whereby the belt is deflected downwardly by a predetermined distance or deflection. The pressure applied to the belt at that time point is measured by using the pressure gauge itself. Mechanical devices for measuring drive belt tension thus are purely mechanical and clamp on to a short section of the belt and predict tension either by applying a known force and measuring belt deflection, or by applying a known deflection and measuring force. Through tests carried out in the laboratory using a tensile testing machine we have shown that these devices give both poor accuracy and poor repeatability of results. Measuring errors of up to 60% can occur in a random manner. One of the reasons why error occurs is that, if the belt slips by even a small amount where it is clamped, this will significantly alter the force/deflection characteristic.

As discussed in U.S. Pat. No. 5,877,431, tension measurement for a flexible member such as the belt employed in association with a power transmission such as that of the engine of a motor vehicle, can use a string tension measuring technique adopted in a process for tuning a string instrument. FIG. 1 is a block diagram showing schematically an apparatus for measuring a string tension of a musical instrument. A sound generated by vibration of a string of concern is collected by a microphone 1 which converts the sound as caught into an electric acoustic signal which is then outputted to a signal processing unit 2 which serves for processing the acoustic signal supplied from the microphone 1 to thereby measure a natural oscillation or vibration frequency of the string and display the natural (vibration) frequency (also known as the characteristic or proper frequency) in the form of numerical values. To this end, the signal processing unit 2 is comprised of an input signal shaping circuit 21 for shaping waveform of the acoustic signal inputted from the microphone 1 to thereby eliminate noise components, a frequency counter 22 for sampling or quantizing the acoustic signal outputted from the input signal shaping circuit 21 to thereby convert the input signal into a digital signal for the purpose of frequency measurement thereof, a CPU (abbreviation of Central Processing Unit) 23 for processing the frequency data as measured for the numerical display thereof, and a display drive circuit 25 for displaying the frequency data as processed on a display device 24. When a string of a musical instrument such as violin is caused to vibrate under frictional sweeping of a bow, the string vibrates at a frequency intrinsic to the string, whereby a vibration sound is generated, which sound is collected by the microphone 1 to be converted into an electrical acoustic signal. In the signal processing unit 2, the acoustic signal undergoes the waveform shaping processing affected by the input signal shaping circuit 21 for the purpose of noise elimination. The acoustic signal outputted from the signal input shaping circuit 21 is then inputted to the frequency counter 22 to be converted into a corresponding digital signal, from which frequency data is generated by counting the pulses contained in the digital signal. The frequency data is then processed by the CPU 23 to a form suited for a numerical display to be subsequently displayed on the display device 24.

The technique for measuring the natural vibration frequency of the of the string of a musical instrument has been applied to measurement of the natural vibration of a belt employed in the engine for the motor vehicle by collecting the vibration sound generated by the belt by applying a vibration and collecting it by the microphone 1 and processing the acoustic signal by the signal processing unit 2 for displaying the natural vibration frequency of the belt and/or the tension arithmetically determined on the natural vibration frequency in terms of a numerical value. As discussed in U.S. Pat. No. 5,877,431, the apparatus for measuring a tension of a belt in a spanned state includes a vibration detector for detecting a vibration of the belt, a vibration frequency arithmetic unit for arithmetically determining a vibration frequency on the basis of the vibration as detected, and a tester equipped with a display device. The tester includes an information processor for arithmetically determining a tension of the belt on the basis of the vibration frequency supplied from the vibration frequency arithmetic unit and information about the belt read out from a storage medium, and the display device for displaying the result of the arithmetic operation performed by the information processing means. The tension measuring apparatus is then used for detection of a tension of a belt of a car belt transmission.

SUMMARY

Systems and methods for measuring belt tension in a semiconductor processing system include measuring a natural sound or an acceleration of the belt in the semiconductor processing system; digitizing the natural sound or the acceleration; determining the frequency and characterizing the belt tension as a function of the frequency.

A transmission belt's tension can be adjusted using a fixed pulley and a sliding movable second pulley. The belt's tension can be characterized using a sensor, a microphone or accelerometer, a guitar pick and a software system. A method is developed to ensure accurate characterization of the belt's tension by comparing to a known good belt tension characterization table.

Advantages of the system may include one or more of the following. The system enables optimization of belts to transmit power and/or to provide timing synchronization. To provide correct operation, the system enables belts to be set to within a special range of tensions. A belt which is too tight may be likely to suffer excessive wear and deterioration in operation, while a belt which is too loose may slip laterally off a guide pulley, or slip longitudinally, or jump teeth in the case of a ribbed belt. The system assists with the initial setting up of the machine may be setting the belt tension to within an acceptable range of values. The tension in a drive belt which has been installed around pulleys can be easily determined even with limited space that may be available for measuring the tension. The drive belt tension monitoring system achieves better levels of accuracy and repeatability in monitoring.

BRIEF DESCRIPTION OF THE DRAWINGS

The invention will be more fully understood from the description of the preferred embodiment with reference to the accompanying drawings, in which:

Referring now to FIG. 2, an exemplary belt tension analyzer system 100 is shown. The system includes a stationary pulley 102 and a sliding moveable pulley 104. A belt 106 loops on the pulleys 102–104. The belt's tension can be adjusted using the fixed pulley 102 and the sliding movable pulley 104. A sensor 108 measures vibration frequency as pulley 104 is pulled to adjust the belt's tension. The sensor 108 outputs frequency data points. For example, a pick 110 such as a guitar pick is used to produce a natural sound or picking sound. In this embodiment, the system 100 measures the natural vibration (also known as the characteristic or proper vibration frequency) of the belt which occurs upon application of impulsive shock to the belt. In one embodiment, the sensor 108 can be a microphone to pick sound at its resonant frequency. In another embodiment, the sensor 108 can be an accelerometer to pick up vibrational frequency.

The term "natural frequency" as used herein refers to any frequency at which the belt will naturally vibrate. In the normal case this will be the fundamental frequency but it is possible to arrange for the belt to vibrate in harmonic modes at multiples of the fundamental frequency of vibration. The natural frequency at which the belt vibrates provides an accurate and reliable indication of the tension of the belt. Although such belts are of significant thickness and do not therefore vibrate exactly in the manner of a simple string, monitoring the natural frequency of vibration of the drive belt provides a reliable indication of the tension in the belt. The belt may be vibrated by the application of an initial impulse thereto and thereafter be left to vibrate freely, substantially without the influence of external forces. In this case the belt automatically vibrates at a natural frequency.

By imparting a vibration impulse using a pick, for example, the system 100 can determine belt tension by analyzing not only the noise or sounds generated by the belt but also the vibration or energy spectra thereof. The system display vibration characteristics as well as degree of fatigue of the belt on the basis of the result of the analysis in the form of graphics or corresponding message on a display. A microphone 112 captures the picking sound. The outputs of the sensor 108 and the microphone 112 are digitized by a processor. The digitization is typically done using an analog to digital converter after suitable analog filtering and pre-processing. The processor processes the signal and outputs a frequency analysis. The process is repeated to map a relationship between tension and belt frequency. For example, in one embodiment, the belt 106 can be characterized based on the determined frequency as follows:

| Force (lbs/in) | Frequency (Hz) |
|---|---|
| 1 | 200 |
| 2 | 250 |
| 3 | 300 |
| 4 | 350 |
| 5 | 400 |

The input data can be detected by a microphone, an accelerometer, a transducer or other detector capable of detecting frequency variations caused by an impulse. The sound wave can be detected through the air, through a semiconductor equipment structure, such as a beam to which the belt tension analyzer is attached. In another microphone embodiment, the microphone is mounted on the belt and an impulse is applied to the belt using a guitar pick. In one accelerometer embodiment, the accelerometer is mounted on the belt and an impulse is applied to the belt using a guitar pick. Frequency analysis is then applied to the digitized sound wave.

Figure 1:
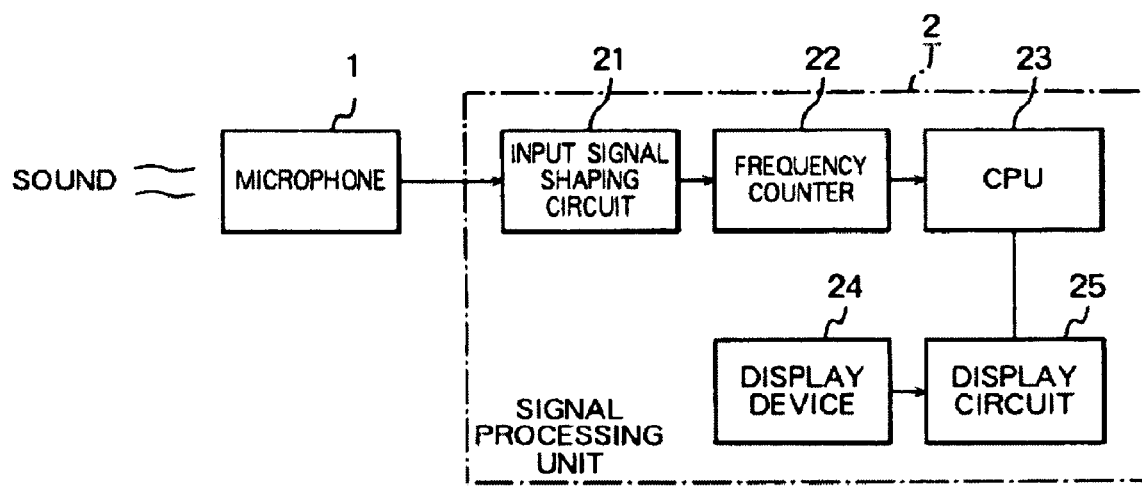
FIG. 1 is a block diagram showing schematically an apparatus for measuring a string tension of a musical instrument.
Figure 2:
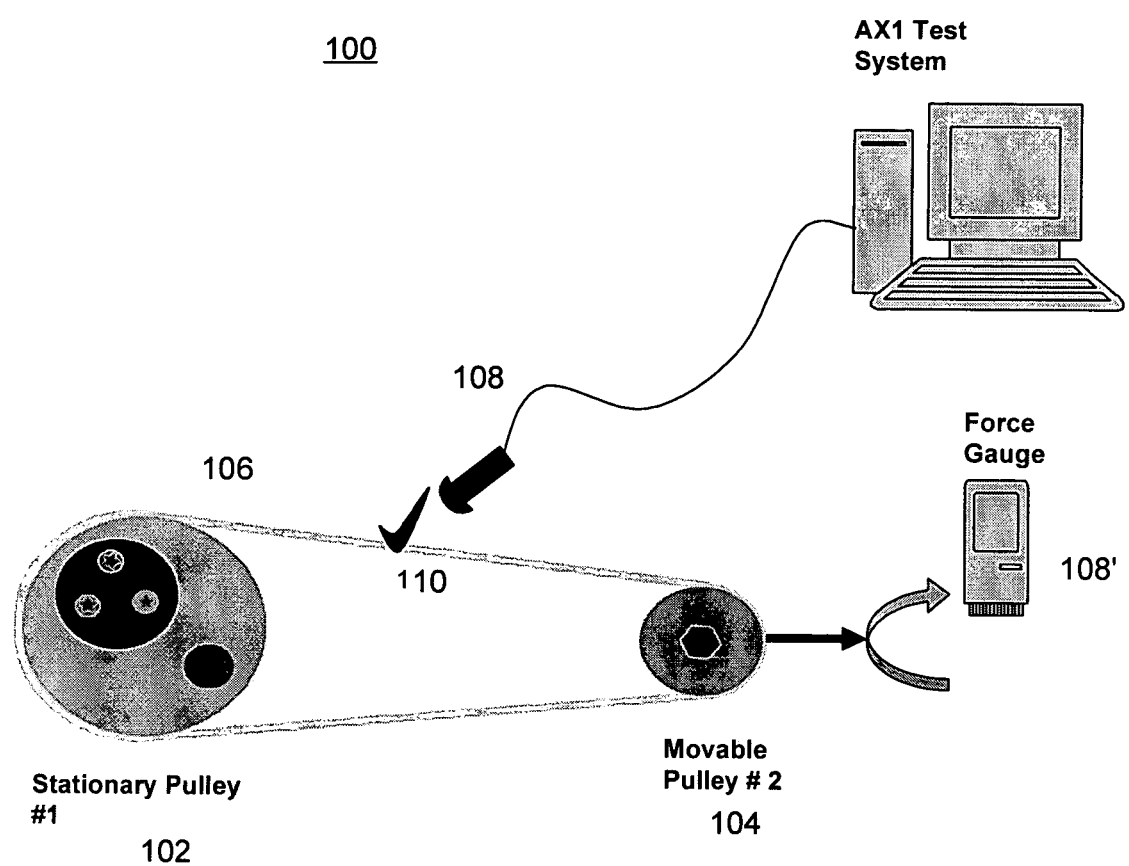
FIG. 2, an exemplary belt tension analyzer system
Figure 3:
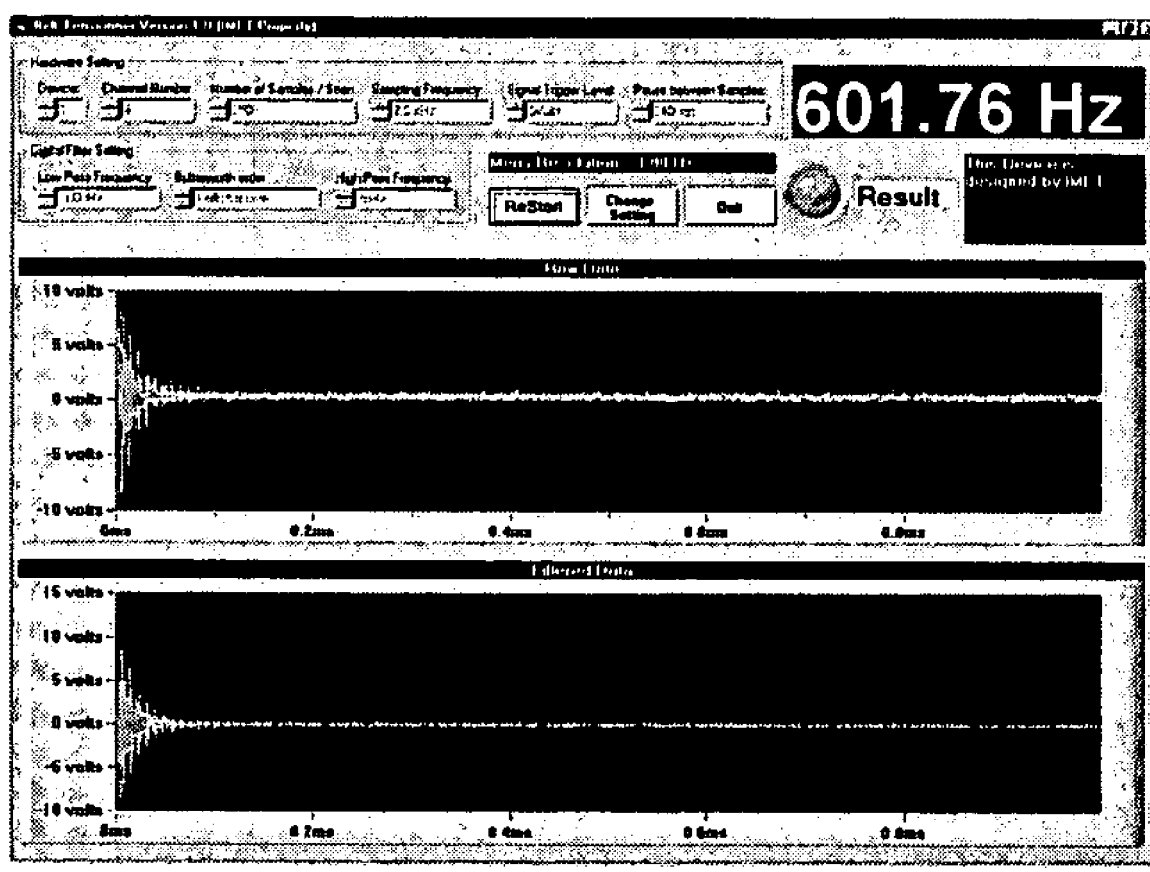
FIG. 3 shows an exemplary frequency analysis system.

FIG. 3 shows an exemplary frequency analysis system for sound frequency analysis. In a PC-based embodiment, the microphone 112 converts sounds into voltage. First, sound is converted to electrical current using a microphone. Continuous oscillations of air pressure become continuous oscillations of voltage in an electrical circuit. This fast-changing voltage is then converted into a series of numbers by a digitizer. A digitizer acts like a very fast digital voltmeter. It makes thousands of measurements per second. Each measurement results in a number that can be stored digitally (that is, only a finite number of significant digits of this number are recorded). This number is called a sample and the whole conversion of sound to a series of numbers is called sampling. A sound card in a computer has a digitizer. When the microphone 112 is plugged in, the sound card will produce a stream of samples that can be retrieved by the frequency analysis software.

The sound card acts as a fast digital voltmeter. It measures the voltage as often as 11,025—up to 44,100 times per second. Each measurement is converted into an 8- or 16-bit number called a sample. 16-bit numbers allow for more accuracy in measuring subtle effects. The result of sampling is a series of numbers. This series is displayed in the upper right pane of the Frequency Analyzer. Every sound can be represented as a combination of sine waves of various frequencies. Mathematically, this splitting into component frequencies is called a Fourier transform. There are many ways of calculating the Fourier transform—some of them faster, some of them slower. The best algorithm invented so far is called the Fast Fourier Transform (FFT). It calculates a Fourier transform of a digital signal using the divide-and-conquer method. It takes a certain number of samples (has to be a power of 2) and calculates the "spectrum," or the intensities of various sine waves that are the components of that sound. Since the sound usually changes with time, the Fourier transform is calculated many times per second. In one embodiment, the FFT transform uses the following equation:

$$A_k = \sum_{n=0}^{N-1} x_n e^{-2\pi i k n/N}$$

In another embodiment, instead of picking up sound, an accelerometer is positioned on the belt at rest. The accelerometer is then actuated with a pick (such as a guitar pick). The output of the accelerometer is captured and processed. In one implementation, Fourier transform is applied to the output of the accelerometer.

In yet another embodiment, a microphone and an accelerometer is positioned on the belt at rest. Both are then actuated with a pick (such as a guitar pick). The outputs of the microphone and accelerometer are captured and processed. Fourier transform is then applied to the collective outputs of the microphone and the accelerometer.

In another embodiment, noise from either the microphone or the accelerometer is removed by filtering the data. In yet another embodiment, a temporal frequency content of noise from either the microphone or the accelerometer is then determined by filtering the noise into at least to frequency bands and detecting the energy (energy content) in the frequency bands. This is done by a filter bank having a filter (at least one frequency filter). In another embodiment the detected noise is digitized. A temporal frequency transform of the digitized signal is then performed to obtain the temporal frequency content. The temporal frequency transform can be accomplished using a short time Fourier transform, wavelet analysis or other temporal frequency transforms. Next the temporal frequency content is analyzed to determine belt tension.

In another embodiment, an accelerometer can be used to detect belt tension by:
1) applying an impulse to the belt;
2) measuring an acceleration of the belt in the semiconductor processing system; and
3) characterizing the belt tension as a function of the acceleration.

Figure 4:
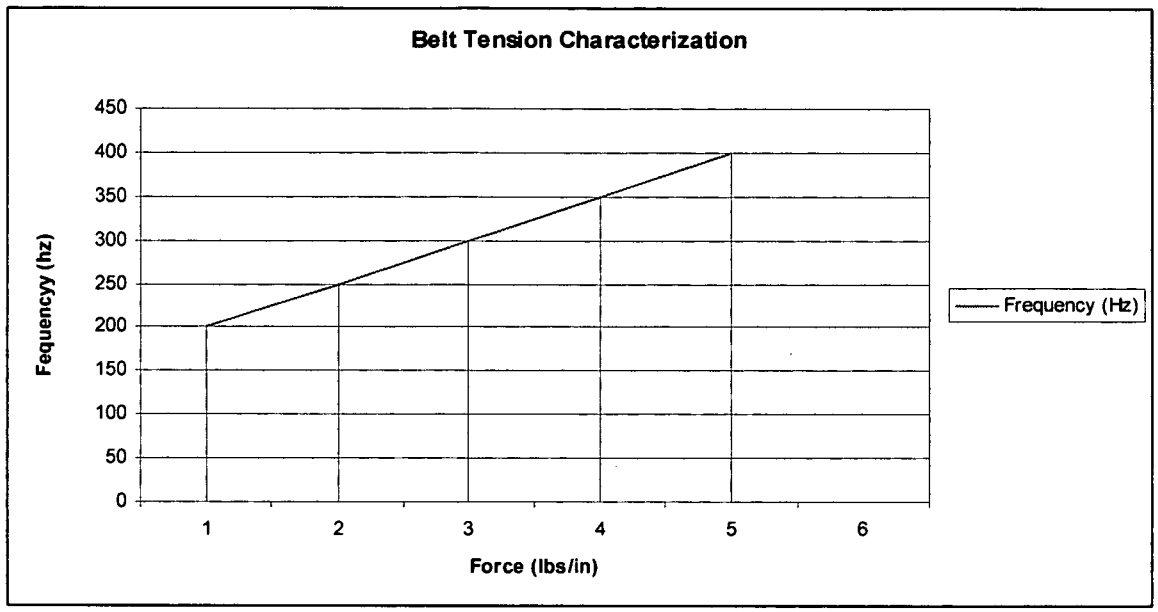
FIG. 4 shows an exemplary belt tension characterization.

The belt's tension can be determined for accuracy by comparing the result to a known good belt tension chart as shown in FIG. 4. As shown therein, a linear relationship exists between a tension force and a determined sound frequency. However, the relationship may be non-linear as well. A user can plot the various frequency responses against the force exerted and determine whether the belt needs to be replaced. Alternatively, instead of displaying the belt tension in the manner described in FIG. 4, it is possible to display on the display device of the tester a graph indicative of the analogue values on a time-serial basis by fetching the frequency values in succession. In that case, the degree of fatigue which the belt suffers as well as the timing for exchanging the belt with a fresh one in the future can be estimated.

In another embodiment, an exemplary belt tension analyzer system can use an accelerometer in place of the microphone 112. As discussed before, the system includes the stationary pulley 102 and the sliding moveable pulley 104. The belt 106 loops on the pulleys 102–104. The belt's tension can be adjusted using the fixed pulley 102 and the sliding movable pulley 104. The sensor 108 measures the force as pulley 104 is pulled to adjust the belt's tension. The sensor 108 outputs a force data point. At a given force data point, a pick 110 such as a guitar pick is used to impart an impulse on the belt 106. In this embodiment, the system measures the acceleration (also known as the characteristic or proper vibration frequency) of the belt which occurs upon application of impulsive shock to the belt. By imparting a vibration analysis, the system 100 can determine belt tension by analyzing the acceleration. The outputs of the sensor 108 and the accelerometer are digitized by a processor. The digitization is typically done using an analog to digital converter after suitable analog filtering and pre-processing. The processor processes the signal and outputs a frequency analysis. The process is then repeated to map a relationship between tension and belt frequency.

The invention has been described in terms of specific examples which are illustrative only and are not to be construed as limiting. The invention may be implemented in digital electronic circuitry or in computer hardware, firmware, software, or in combinations of them. Apparatus of the invention may be implemented in a computer program product tangibly embodied in a machine-readable storage device for execution by a computer processor; and method steps of the invention may be performed by a computer processor executing a program to perform functions of the invention by operating on input data and generating output. Suitable processors include, by way of example, both general and special purpose microprocessors. Storage devices suitable for tangibly embodying computer program instructions include all forms of non-volatile memory including, but not limited to: semiconductor memory devices such as EPROM, EEPROM, and flash devices; magnetic disks (fixed, floppy, and removable); other magnetic media such as tape; optical media such as CD-ROM disks; and magneto-optic devices. Any of the foregoing may be supplemented by, or incorporated in, specially-designed application-specific integrated circuits (ASICs) or suitably programmed field programmable gate arrays (FPGAs).

From the aforegoing disclosure and certain variations and modifications already disclosed therein for purposes of illustration, it will be evident to one skilled in the relevant art that the present inventive concept can be embodied in forms different from those described and it will be understood that the invention is intended to extend to such further variations. While the preferred forms of the invention have been shown in the drawings and described herein, the invention should not be construed as limited to the specific forms shown and described since variations of the preferred forms will be apparent to those skilled in the art. Thus the scope of the invention is defined by the following claims and their equivalents.

What is claimed is:

1. A method for measuring belt tension in a semiconductor processing system, comprising:
 measuring a natural sound of a static belt in the semiconductor processing system;
 filtering the natural sound to remove noise;
 determining the natural sound frequency for the static belt in the semiconductor processing system; and
 characterizing the belt tension as a function of the frequency and force.

2. The method of claim 1, further comprising using the characterized belt tension to maintain the semiconductor processing system.

3. The method of claim 2, wherein the belt is mounted between two pulleys, further comprising adjusting a distance between the pulleys based on the belt tension.

4. The method of claim 1, further comprising picking the belt to generate the natural sound.

5. The method of claim 1, further comprising measuring a force on the belt.

6. The method of claim 1, further comprising comparing the characterized belt tension with a known-good-belt tension.

7. The method of claim 1, further comprising applying a Fourier transform to the sound.

8. A method for measuring belt tension in a semiconductor processing system, comprising:
   applying an impulse to a static belt;
   measuring an acceleration of the belt in the semiconductor processing system in response to the impulse on the static belt; and
   characterizing the belt tension as a function of the acceleration.

9. The method of claim 8, further comprising using the characterized belt tension to maintain the semiconductor processing system.

10. The method of claim 9, wherein the belt is mounted between two pulleys, further comprising adjusting a distance between the pulleys based on the belt tension.

11. The method of claim 8, further comprising picking the belt to generate the acceleration.

12. The method of claim 8, further comprising measuring a force on the belt.

13. The method of claim 8, further comprising comparing the characterized belt tension with a known-good-belt tension.

14. The method of claim 8, further comprising applying a Fourier transform to data on acceleration.

15. An apparatus for measuring belt tension in a semiconductor processing system, comprising:
   an accelerometer mounted on a static belt to capture a vibration on the belt in the semiconductor processing system;
   an analog to digital converter coupled to the accelerometer;
   a processor coupled to the ADC to determine an acceleration frequency and to characterize the belt tension as a function of the frequency and force.

16. The apparatus of claim 15, wherein the characterized belt tension is used to maintain the semiconductor processing system.

17. The apparatus of claim 16, wherein the belt is mounted between two pulleys in the semiconductor processing system and wherein the pulleys are adjusted based on the belt tension.

18. The apparatus of claim 15, further comprising a guitar pick to apply an impulse to the belt to generate the natural sound.

19. The apparatus of claim 15, further comprising a sensor to measure a force on the belt.

20. The apparatus of claim 15, further comprising:
   a microphone to capture a natural sound of a static belt in the semiconductor processing system;
   an analog to digital converter coupled to the microphone to digitize the natural sound;
   wherein the processor is coupled to the ADC to determine the natural sound frequency and to characterize the belt tension as a function of the frequency.

* * * * *